United States Patent [19]  
Bellinson

[11] Patent Number: 4,942,882  
[45] Date of Patent: Jul. 24, 1990

[54] METHOD AND APPARATUS FOR MONITORING DESCENT OF FETUS

[76] Inventor: Susan Bellinson, 99 A Schofeld St., City Island, N.Y. 10464

[21] Appl. No.: 175,965

[22] Filed: Mar. 31, 1988

[51] Int. Cl.$^5$ .............................................. A61B 5/10
[52] U.S. Cl. .................................... 128/775; 128/642; 128/778
[58] Field of Search ............... 128/642, 337, 778, 775; 33/511, 512; 604/117, 93, 271; 24/467, 531

[56] References Cited

U.S. PATENT DOCUMENTS

| Re. 28,990 | 10/1976 | Hon et al. ........................ 128/2.06 E |
| 1,054,802 | 3/1913 | Spiro ..................................... 128/775 |
| 1,892,018 | 12/1932 | Stanton ................................. 24/531 |
| 2,394,140 | 12/1943 | Biscon .................................. 33/512 |
| 3,643,651 | 2/1972 | Cuadros ................................ 33/512 |
| 3,938,504 | 2/1976 | Dickinson, III et al. ............. 33/512 |
| 4,320,764 | 3/1982 | Hon . | |
| 4,362,167 | 12/1982 | Nicolai et al. ...................... 128/778 |
| 4,476,871 | 10/1984 | Hon ..................................... 128/642 |

FOREIGN PATENT DOCUMENTS 7900078  4/1980  France ................................. 128/778

OTHER PUBLICATIONS

Hunter et al., *A Technic for Recording Fetal ECG During Labor and Delivery*, vol. 16, No. 5, Obstetrics & Gynecology, 567–570 (Nov. 1960).

Hon, *Apparatus for Continuous Monitoring of the Fetal Heart Rate*, vol. 32, No. 5, Yale Journal of Biology & Medicine, 397 (Apr. 1960).

*Primary Examiner*—Max Hindenburg  
*Assistant Examiner*—Scott Getzow  
*Attorney, Agent, or Firm*—Christopher B. Garvey

[57] ABSTRACT

A method and apparatus for monitoring the location of a fetus in a birth canal during labor. The conductors of a fetal monitor probe, such as a fetal heartbeath monitor electrode, are marked with calibration means corresponding to pedetermined distances from a babyward end of the probe. The babyward end of the probe is attached to the baby. During labor, the position and progress of the fetus in the birth canal may be inferred by observing the calibration means relative to the outer end of the birth canal.

5 Claims, 6 Drawing Sheets

METHOD AND APPARATUS FOR MONITORING DESCENT OF FETUS

FIELD OF INVENTION

The present invention relates to an improvement in fetal monitor probes, particularly fetal heartbeat monitors.

It has long been recognized that monitoring fetal heartbeat is an important procedure during the conduct of labor. Various methods and apparatus for performing this monitoring function have been designed over the years. For example, U.S. Pat. Re. No. 28,990 for a *Bipolar Electrode Structure For Monitoring Fetal Heartbeat And The Like*, reissued to Hon et al on Oct. 5, 1976, dates back to an application filed in January of 1971. That patent refers in column 1, lines 34-40 to an article in Vol. 16, No. 5 of *Obstetrics and Gynecology*, (November 1960), pages 567-570. U.S. Pat. No. 3,580,242, for a *Fetal Scalp Electrode*, issued to LaCroix on May 25, 1971 refers to *Hon, Yale Journal of Biology and Medicine*, Vol. 32, No. 5, page 397 (April 1960), describing an electrode encased in plastic tubing. Thus, fetal heartbeat monitor electrode probes have been known for at least twenty-seven years.

Another important part of monitoring labor is assessment of cervical changes including the location of the fetal presenting part as it descends through the birth canal. Conventionally, this has been assessed by inserting an examiner's fingers into the birth canal. Such examinations have been practiced for many decades, possibly even for centuries. While there are advantages to knowing the degree of fetal descent during labor, frequent examinations increase the risk of infection, may be uncomfortable for the patient, require a skilled examiner, and consume costly supplies such as examination gloves, lubricant or antiseptic.

The object of the present invention is to use the conductors of a fetal monitor probe to indicate the descent of the fetus without frequent vaginal examinations.

BRIEF DESCRIPTION

The present invention is an improvement to a fetal monitor probe, particularly a fetal scalp electrode heartbeat monitor, comprising distance calibration means marked on the conductors of a fetal monitor probe. There are several alternative calibration means possible.

In one embodiment, the calibration means comprise a plurality of regions of different colors. Each color corresponds to a predetermined number of centimeters from the babyward end of the probe. A legend showing which color corresponds to which distance would be printed on the package or package insert for convenient reference. In practice, the probe would be inserted into the birth canal and attached to the fetus. A gentle traction or outward tension would be applied to the wires of the probe which serve as the conductor means for a sensor such as an electrode. The color protruding at the outward end of the birth canal would be observed by the delivery-room personnel. Reference to the convenient legend on the package would quickly tell said personnel how many centimeters from a reference point, such as the outward end (vaginal introitus) of the birth canal, the fetus was located.

Alternatively, the wires could be encased in a jacket of sufficient thickness to print actual numbers on. Thus, the jacketing could be graduated in centimeters similarly to a meter stick.

Alternatively, thin marks could be made on the conductor means in a coded system. Another approach would be to apply colored or distinctively sized silicone beads to the conductors.

A conventional probe could be calibrated in the delivery-room by slipping a calibrated sheath over the conductors.

A moveable clip could also be used to mark the starting position at the vaginal introitus.

A simple means which might be adopted by delivery-room personnel to a conventional probe would be to affix a single tape mark on the conductors at a premeasured distance from the babyward end of the probe along the conductors. By subtracting the exposed distance between an accessible reference point, such as the vaginal introitus, and the tape mark from the known premeasured distance between said mark and the babyward end of the probe, the depth of the fetus in the birth canal could be inferred.

A primary advantage of the present invention is that it would allow an observer to estimate the degree of descent of the fetus through the birth canal without performing repeated vaginal examination. There are several advantages to knowing the degree of fetal descent during labor without performing repeated vaginal examinations, including reduced risk of infection, reduced risk of chorioamnionitis, reduced discomfort to the patient, reduced need for the frequent attention of a skilled examiner and reduced consumption of costly supplies such as examination gloves, lubricant or antiseptic. In addition, the invention would provide a warning indication to even an unskilled observer if descent were occurring unusually rapidly. This warning would allow appropriate preparations for delivery to be made. As a further advantage, reasons for sudden decelerations in the fetal heart rate might be more readily assessed if the attendant could see that rapid descent had taken place, since such rapid descent can cause bradycardia. The present invention also allows the quality of maternal pushing efforts in the second stage of labor to be more readily assessed without vaginal examination. Furthermore, the progress of descent in the second stage of labor can be assessed visually. Finally, the present invention would serve as a useful teaching tool for examiners who could compare their examination findings with another objective measurement of descent.

DETAILED DESCRIPTION OF PREFERRED EMBODIMENT

Figure 1:
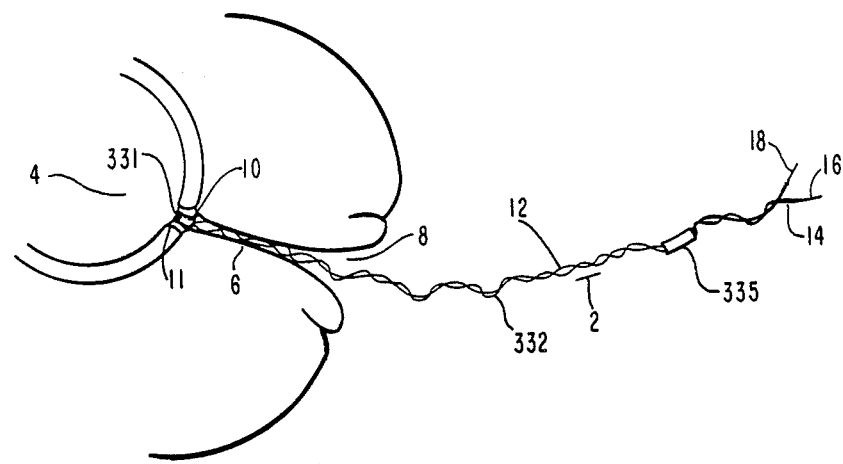
FIG. 1 is a top view of a fetal heartbeat monitor probe showing its environment in section.

Referring now to the drawings, FIG. 1 shows a fetal heartbeat monitor probe, generally designated 2, in its operating environment. Said environment is shown in section and includes the fetal presenting part (shown here as fetal head 4), birth canal 6, and the outer end 8 of birth canal 6 termed "vaginal introitus" 8. Probe 2 may be any fetal monitor probe. One popular type is shown in Hon et al, U.S. Pat. No. 28,990, referred to above, the disclosure of which is hereby incorporated by reference. Said probe has a probe head 10 at its babyward end 11, conductor means such as conductors 12 comprising a pair of insulated twisted wires which terminate at an outer end 14 at which the insulation has been stripped from the bare conductors 16, 18 (FIG. 2).

Figure 2:
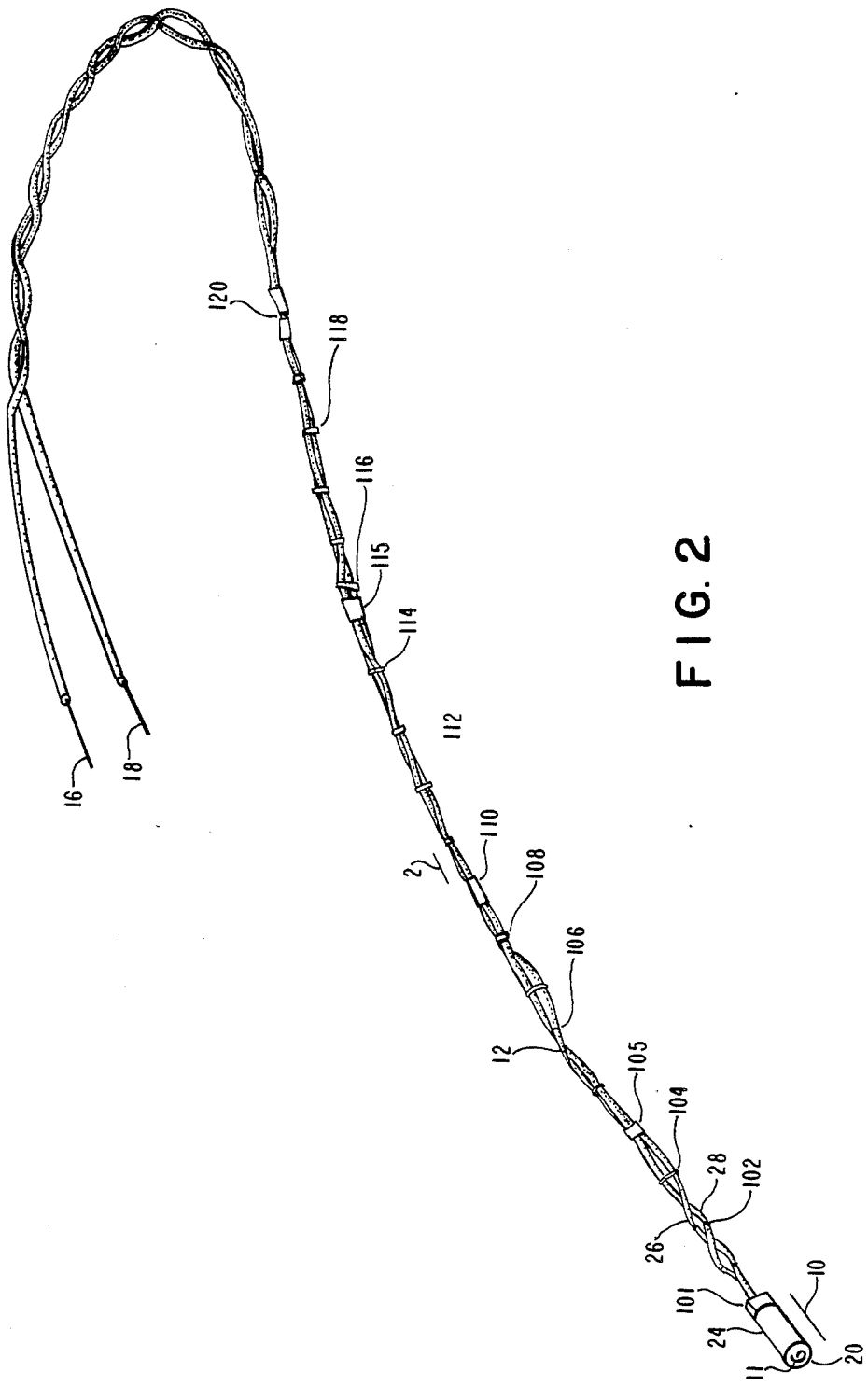
FIG. 2 is an oblique view of an improved probe of the present invention, showing calibration means.

FIG. 2 is an oblique view of an improved probe of the preferred embodiment. Probe head 10 comprises a sensor, such as spiral scalp electrode 20 mounted on a holder 24 which in turn is mounted to conductors 12 comprising a pair of wires 26 and 28. Marks 101-120 are provided at 1 centimeter intervals from babyward end 11. Five-centimeter mark 105 is double the thickness of an ordinary mark such as 102-104. Ten-centimeter mark 110 is double the thickness of mark 105. Mark 115 comprises two distinct marks, one being the thickness of ten-centimeter mark 110 and the second being the thickness of five-centimeter mark 105. Twentycentimeter mark 120 comprises two marks each of the thickness of ten-centimeter mark 110. As a further means of communicating distance, color is used. The region between end 11 and mark 102 would be violet. From mark 102 to mark 104 would be red. Color would change every two centimeters according to the following table:

TABLE 1

Figure 3:
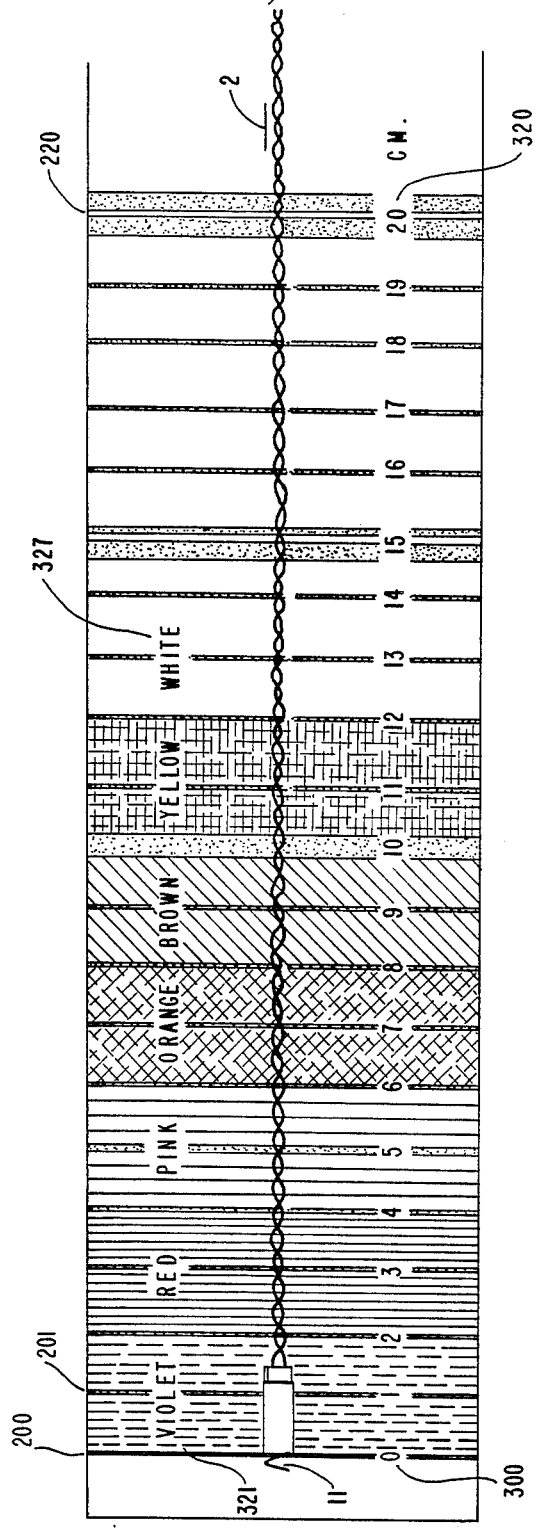
FIG. 3 is a diagrammatic legend such as would be printed on the package or package insert of a fetal probe.

| Distance in Centimeters | Color of Region | Mark No. in FIG. 3 |
| --- | --- | --- |
| 0-2 | Violet | End 11 to mark 102 |
| 2-4 | Red | 102-104 |
| 4-6 | Pink | 104-106 |
| 6-8 | Orange | 106-108 |
| 8-10 | Brown | 108-110 |
| 10-12 | Yellow | 110-112 |
| 12-end | White | 112 et seq. |

FIG. 3 is a diagrammatic legend such as would be printed on a package containing the improved monitor or on a package insert. Colors are depicted in FIG. 3 by means of conventional linings as shown in the color chart in 37 CFR Section 2.52(e). The actual legend would be printed in color. This legend comprises marks 201-220 corresponding to the marks 101-120 shown in FIG. 2 on the probe. As in FIG. 3, probe 2 is depicted stretched along these marks from probe end 11 at mark 200 past mark 220. Numerals 300-320 designate the distances from probe end 11 by arabic numbers "0-20" printed upon marks 200-220. Words 321 are also printed on the legend, describing the colors.

The method of the present invention (FIG. 1) involves attaching babyward end 11 of probe 2 to a point 331 on the scalp of fetal head 4 in the conventional manner. Once the probe is attached to the fetus, a gentle traction is applied to an outer part such as 332 of conductors 12 in an outward direction, thus making sure that the conductors 12 are extended to their measured length. The location of the presenting end of the fetus at attachment point 331 can thereafter be inferred by simply observing the marks 101-120 and colors, outlined in Table 1 and depicted in FIG. 3, and by referring to the legend on the package or insert depicted in FIG. 3. The mark or color at a reference point such as vaginal introitus 8 corresponds to the distance of fetal attachment point 331 from that reference point. Gentle traction on the conductors, as described above, is recommended prior to each observation.

Figure 4:
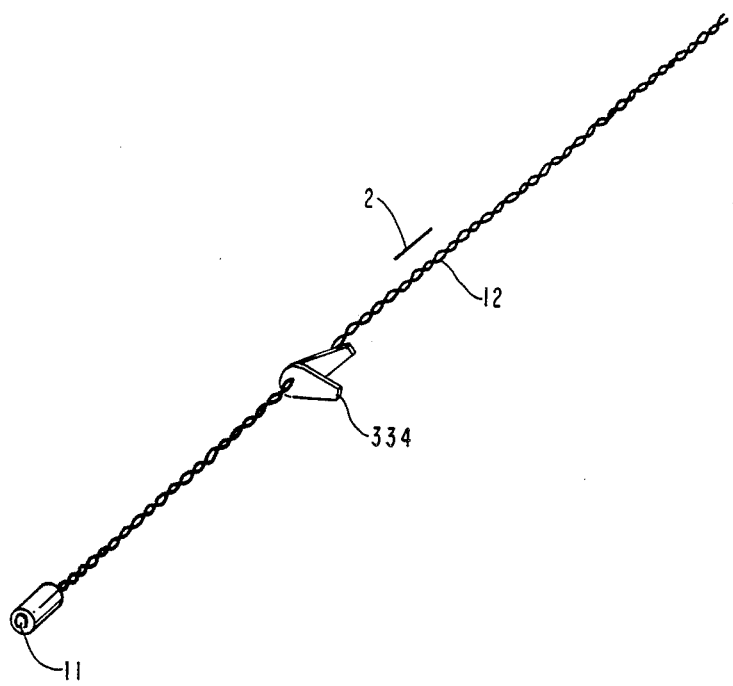
FIG. 4 is an oblique view of an alternative embodiment.

FIG. 4 shows an alternative embodiment which may be used by delivery-room personnel with a conventional probe. First, the probe is conventionally attached to the fetus. Next, marking means, such as spring-clip 334, may be set on conductors 12 at a reference point such as the vaginal introitus 8 (FIG. 1) to give a relative indication of progress from a starting point. A plastic centimeter ruler can be provided in the package to measure this distance.

Alternatively (FIG. 1), the marking means can be a piece of tape 335 attached to conductors 12 at a premeasured distance from babyward end 11 of probe 2. Probe 2 is then conventionally attached to fetal head 4 as in FIG. 1. By subtracting the distance between tape 335 and the vaginal entroitus 8 from the premeasured distance between tape 335 and babyward end 11, the location of the fetal head 4 in the birth canal 6 may be inferred.

Figure 5:
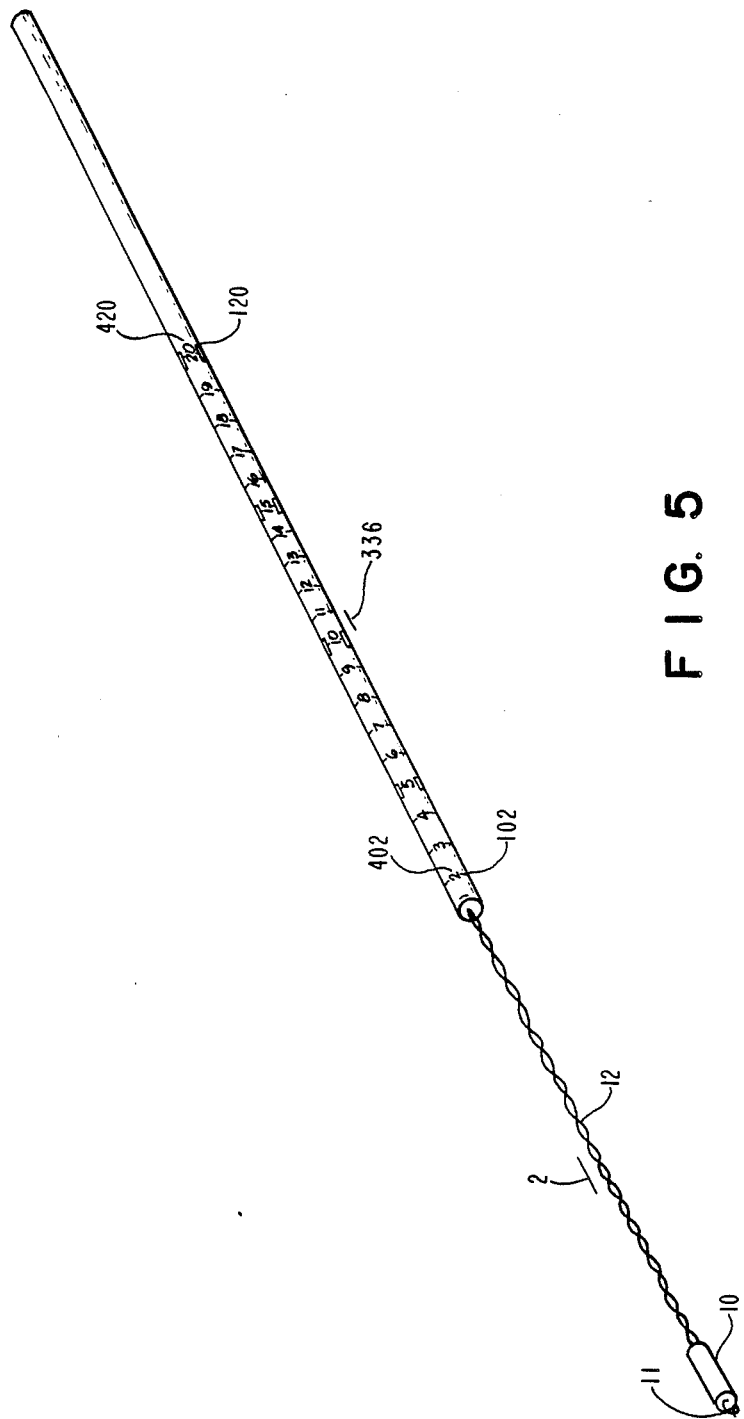
FIG. 5 is an oblique view of another alternative embodiment.

FIG. 5 shows a calibrated sheath 336 which may be slipped over the conductor means 12 of a conventional probe 2 by delivery-room personnel. The sheath is made to abut probe head 10. With the probe in its working position, the position of the fetus may be inferred by reading numerals 402-420, marks 102-120, or the colors as described above.

Figure 6:
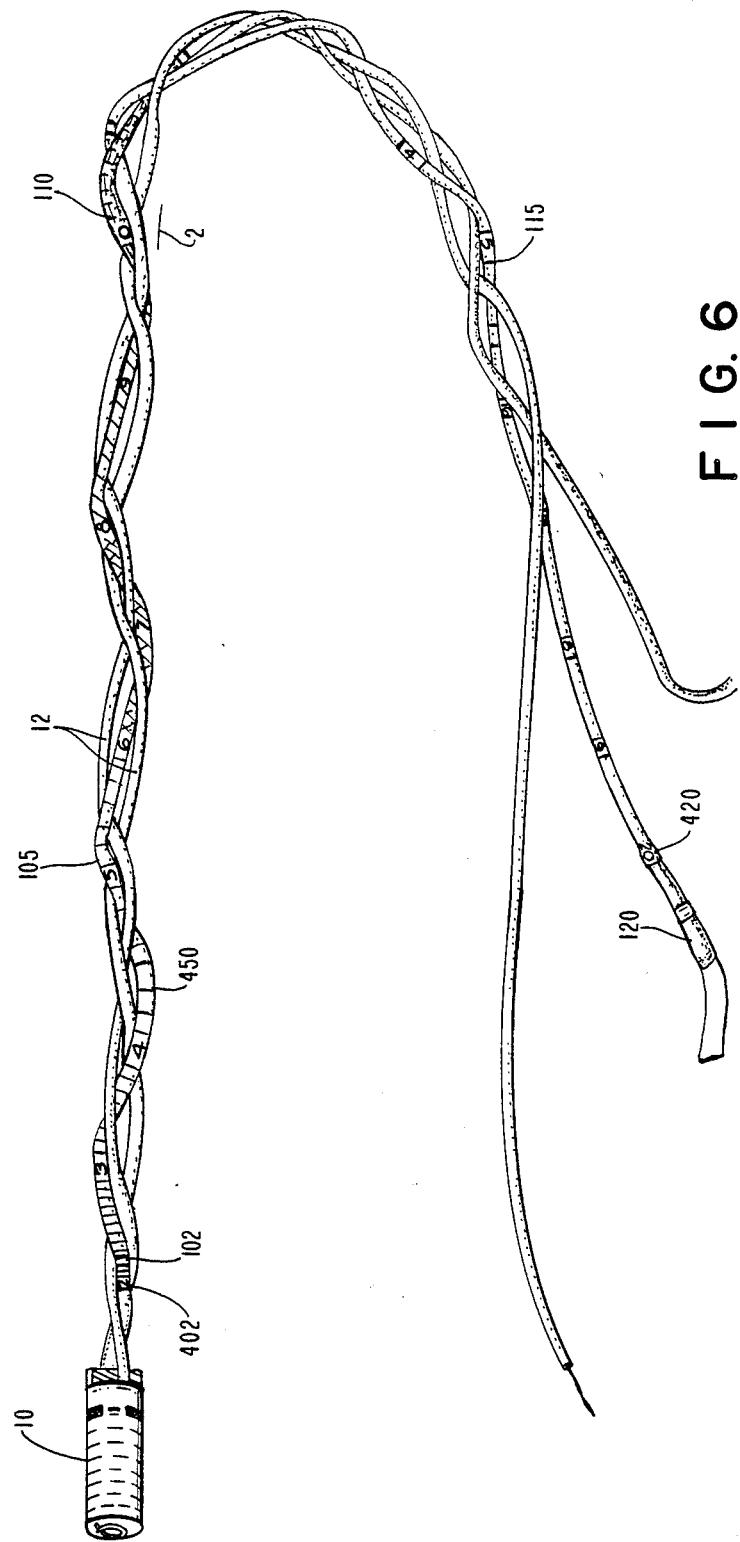
FIG. 6 is an oblique view of still another alternative embodiment.

FIG. 6 shows the calibration means as a calibrated measuring line means, such as a measuring tape 450, affixed to the probe head 10 and included with the conductors 12 by entwining the tape into their spiral as shown, or simply by running the tape alongside the conductors. The tape would be marked with marks 102-120, colors, or numerals 402-420, similarly to sheath 336 described above and shown in FIG. 5.

I claim:

1. An apparatus for use as a fetal heartbeat monitor probe in a birth canal said probe having a babyward portion and an outward portion, said probe comprising:
   a probe head, at the babyward portion of the probe, said probe head having a babyward end, the babyward end of said probe head having wire attachment means for attaching the probe head to a fetus;
   thin flexible wire conductor means for connecting to the probe head through the birth canal, a babyward part of which conductor means is connected to the probe head, an outward part of which comprises the outward portion of the probe;
   said conductor means including calibration means for measuring distance from the babyward end of the probe and monitoring the location of the fetus in the birth canal.

2. A method of monitoring location of a moving fetus in a birth canal comprising the steps of:
   attaching a babyward end of a fetal monitor probe to the fetus, said probe having thin flexible wire conductor means connecting said babyward end through the birth canal; and having calibration means thereon
   applying traction to the conductor means to extend them and the calibration means to their full length;
   observing said calibration means along the conductor means located at a reference point such as a vaginal introitus; and
   determining the location of the fetus from a known distance corresponding to the calibration means located at the reference point.

3. A method of monitoring location of a moving fetus in a birth canal comprising the steps of:
   placing a calibration mark at a known distance from a babyward end of a fetal monitor probe located along thin flexible wire conductor means which are part of said probe;
   attaching the babyward end of said probe to the fetus through the birth canal;
   applying traction to the conductor means to extend them to their full length;
   observing a distance between the calibration mark and a reference point such as a vaginal introitus; and
   determining therefrom the location of the fetus in the birth canal;

4. A method of monitoring progress of a fetus in a birth canal comprising the steps of:
   attaching a babyward end of a fetal monitor probe to the fetus;
   placing a calibration means along a thin flexible wire conductor means of the fetal monitor probe at a point of reference such as a vaginal introitus;
   applying traction to the conductor means to extend them and the calibration means to their full length;
   observing changes in the position of the calibration means relative to the point of reference; and
   determining therefrom the progress of the fetus in the birth canal.

5. A method of monitoring progress of a fetus in a birth canal comprising the steps of:
   attaching a babyward end of a fetal monitor probe to the fetus;
   observing a calibration means located along a thin flexible wire conductor means of the fetal monitor probe with reference to a point of reference such as a vaginal introitus;
   applying traction to the conductor means to extend them and the calibration means to their full length;
   observing changes in the position of the calibration means relative to the point of reference; and
   determining therefrom the progress of the fetus in the birth canal.

* * * * *